(12) United States Patent
Holloway et al.

(10) Patent No.: US 7,758,629 B2
(45) Date of Patent: *Jul. 20, 2010

(54) FLEXIBLE STENT AND METHOD OF MAKING THE SAME

(75) Inventors: Ken A. Holloway, Tracy, CA (US); Christofer T. Christoforou, Pleasanton, CA (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/371,691

(22) Filed: Mar. 8, 2006

(65) Prior Publication Data

US 2006/0155364 A1    Jul. 13, 2006

Related U.S. Application Data

(62) Division of application No. 10/108,778, filed on Mar. 26, 2002, now Pat. No. 7,288,111.

(51) Int. Cl.
*A61F 2/06* (2006.01)
*A61F 2/02* (2006.01)

(52) U.S. Cl. .................................. 623/1.16; 623/23.75

(58) Field of Classification Search ......... 623/1.15–1.2, 623/1.23, 1.16, 1.38, 23.75, 1.13
See application file for complete search history.

(56) References Cited

U.S. PATENT DOCUMENTS

| | | | | |
|---|---|---|---|---|
| 2,127,903 A | * | 8/1938 | Bowen | 606/154 |
| 3,174,851 A | | 3/1965 | Buehler et al. | |
| 3,868,956 A | | 3/1975 | Alfidi et al. | |
| 4,494,531 A | | 1/1985 | Gianturco | |
| 4,580,568 A | | 4/1986 | Gianturco | |
| 4,604,762 A | * | 8/1986 | Robinson | 623/1.44 |
| 4,731,073 A | * | 3/1988 | Robinson | 623/1.44 |
| 4,733,665 A | | 3/1988 | Palmaz | |
| 4,850,999 A | * | 7/1989 | Planck | 623/1.44 |
| 4,872,220 A | * | 10/1989 | Haruvy et al. | 2/243.1 |
| 4,941,870 A | * | 7/1990 | Okada et al. | 600/36 |
| 5,123,917 A | * | 6/1992 | Lee | 623/22.26 |
| 5,146,391 A | * | 9/1992 | MacFarlane et al. | 361/525 |
| 5,153,820 A | * | 10/1992 | MacFarlane et al. | 361/525 |
| 5,336,599 A | * | 8/1994 | Kitajima | 435/15 |
| 5,389,106 A | | 2/1995 | Tower | |

(Continued)

FOREIGN PATENT DOCUMENTS

EP    1 010 406    6/2000

(Continued)

OTHER PUBLICATIONS

U.S. Appl. No. 10/017,693, filed Dec. 14, 2001, Holloway et al.

(Continued)

*Primary Examiner*—Alvin J Stewart
(74) *Attorney, Agent, or Firm*—Squire, Sanders & Dempsey L.L.P.

(57) ABSTRACT

A stent that can be made of self-expandable members and balloon expandable members is described. The members can be held together by a polymer layer, polymer rings or discreet polymer connectors. Methods of making and using the stent are also described.

13 Claims, 5 Drawing Sheets

U.S. PATENT DOCUMENTS

| | | | | |
|---|---|---|---|---|
| 5,527,353 | A * | 6/1996 | Schmitt | 623/1.44 |
| 5,607,444 | A * | 3/1997 | Lam | 606/194 |
| 5,628,788 | A * | 5/1997 | Pinchuk | 623/1.2 |
| 5,683,448 | A | 11/1997 | Cragg | |
| 5,693,085 | A * | 12/1997 | Buirge et al. | 623/1.13 |
| 5,723,004 | A * | 3/1998 | Dereume et al. | 623/1.35 |
| 5,749,880 | A * | 5/1998 | Banas et al. | 606/198 |
| 5,776,182 | A * | 7/1998 | Bruchman et al. | 623/1.15 |
| 5,779,729 | A | 7/1998 | Severini | |
| 5,788,626 | A * | 8/1998 | Thompson | 623/1.15 |
| 5,824,049 | A * | 10/1998 | Ragheb et al. | 623/1.44 |
| 5,866,217 | A | 2/1999 | Stenoien et al. | |
| 6,010,530 | A * | 1/2000 | Goicoechea | 623/1.13 |
| 6,039,755 | A * | 3/2000 | Edwin et al. | 623/1.15 |
| 6,075,180 | A * | 6/2000 | Sharber et al. | 623/11.11 |
| 6,117,538 | A * | 9/2000 | Hirata et al. | 428/315.9 |
| 6,124,523 | A * | 9/2000 | Banas et al. | 623/1.15 |
| 6,139,573 | A * | 10/2000 | Sogard et al. | 623/1.13 |
| 6,156,064 | A * | 12/2000 | Chouinard | 623/1.44 |
| 6,162,245 | B1 | 12/2000 | Jayaraman | |
| 6,165,212 | A | 12/2000 | Dereume et al. | |
| 6,168,621 | B1 * | 1/2001 | Vrba | 623/1.2 |
| 6,206,915 | B1 * | 3/2001 | Fagan et al. | 623/1.42 |
| 6,245,100 | B1 * | 6/2001 | Davila et al. | 623/1.13 |
| 6,245,102 | B1 | 6/2001 | Jayaraman | |
| 6,258,117 | B1 * | 7/2001 | Camrud et al. | 623/1.16 |
| 6,273,910 | B1 | 8/2001 | Limon | |
| 6,283,991 | B1 * | 9/2001 | Cox et al. | 623/1.13 |
| 6,312,457 | B1 * | 11/2001 | DiMatteo et al. | 623/1.13 |
| 6,315,708 | B1 | 11/2001 | Salmon et al. | |
| 6,315,791 | B1 * | 11/2001 | Gingras et al. | 623/1.13 |
| 6,342,067 | B1 | 1/2002 | Mathis et al. | |
| 6,355,055 | B1 * | 3/2002 | Waksman et al. | 623/1.13 |
| 6,364,904 | B1 | 4/2002 | Smith | |
| 6,383,214 | B1 | 5/2002 | Banas et al. | |
| 6,395,023 | B1 | 5/2002 | Summers | |
| 6,398,803 | B1 * | 6/2002 | Layne et al. | 623/1.13 |
| 6,409,755 | B1 * | 6/2002 | Vrba | 623/1.2 |
| 6,451,047 | B2 | 9/2002 | McCrea et al. | |
| 6,458,152 | B1 | 10/2002 | Khosravi et al. | |
| 6,479,374 | B1 * | 11/2002 | Ioka et al. | 438/601 |
| 6,485,510 | B1 * | 11/2002 | Camrud et al. | 623/1.16 |
| 6,537,310 | B1 | 3/2003 | Palmaz et al. | |
| 6,540,773 | B2 | 4/2003 | Dong | |
| 6,540,776 | B2 | 4/2003 | Sanders et al. | |
| 6,572,651 | B1 * | 6/2003 | De Scheerder et al. | 623/1.44 |
| 6,579,314 | B1 * | 6/2003 | Lombardi et al. | 623/1.44 |
| 6,613,084 | B2 | 9/2003 | Yang | |
| 6,626,938 | B1 * | 9/2003 | Butaric et al. | 623/1.28 |
| 6,699,276 | B2 * | 3/2004 | Sogard et al. | 623/1.13 |
| 6,699,280 | B2 * | 3/2004 | Camrud et al. | 623/1.16 |
| 6,709,455 | B1 | 3/2004 | Chouinard | |
| 6,752,826 | B2 * | 6/2004 | Holloway et al. | 623/1.13 |
| 6,790,228 | B2 * | 9/2004 | Hossainy et al. | 623/1.46 |
| 6,929,659 | B2 * | 8/2005 | Pinchuk | 623/1.13 |
| 7,022,135 | B2 * | 4/2006 | Zilla et al. | 623/1.39 |
| 7,258,891 | B2 * | 8/2007 | Pacetti et al. | 427/2.24 |
| 7,261,735 | B2 * | 8/2007 | Llanos et al. | 623/1.46 |
| 7,288,111 | B1 * | 10/2007 | Holloway et al. | 623/1.15 |
| 7,387,641 | B2 * | 6/2008 | Schmitt | 623/1.22 |
| 7,500,988 | B1 * | 3/2009 | Butaric et al. | 623/1.16 |
| 7,563,324 | B1 * | 7/2009 | Chen et al. | 118/270 |
| 2001/0049554 | A1 * | 12/2001 | Ruiz et al. | 623/1.44 |
| 2003/0114917 | A1 * | 6/2003 | Holloway et al. | 623/1.13 |

FOREIGN PATENT DOCUMENTS

| | | |
|---|---|---|
| EP | 1 177 780 | 2/2002 |
| GB | 2 092 894 | 8/1982 |
| WO | WO 97/33532 | 9/1997 |
| WO | WO 00/76423 | 12/2000 |

OTHER PUBLICATIONS

Baldus et al., *Treatment of Aortocoronary Vein Graft Lesions With Membrane-Covered Stents*, Circulation, 2000; 102:2024-2027.

Christodoulos Stefanadis et al., *Stents Covered by Autologous Venous Grafts: Feasibility And Immediate And Long-Term Results*, American Heart Journal, Mar. 2000, vol. 139, No. 3, pp. 437-445.

Kasirajan et al., *Delayed onset of ascending paralysis after thoracic aortic stent graft deployment*, Journal of Vascular Surgery, Jan. 2000, vol. 31, No. 1, Part 1, pp. 196-199.

Eldad Rechavia et al., *Biocompatibility of Polyurethane-Coated Stents: Tissue and Vascular Aspects*, Catheterization and Cardiovascular Diagnosis 45:202-207 (1998).

Forrester et al., *A Paradigm for Restenosis Based on Cell Biology: Clues for the Development of New Preventive Therapies*, Journal of the American College of Cardiology, Mar. 1, 1991, vol. 17, No. 3, pp. 758-769.

Masakiyo et al., *Restenosis After Percutaneous Transluminal Coronary Angioplasty: Pathologic Observations in 20 Patients*, Journal of the American College of Cardiology, Feb. 1991, vol. 17, No. 2, pp. 433-439.

Monnier et al., *The Use of the Covered Wallstent for the Palliative Treatment of Inoperable Tracheobronchial Cancers*, Chest, Nov. 1996; 110:5:1161-68.

Schellhammer et al., *Polyethylene Terephthalate And Polyurethane Coatings For Endovascular Stents: Preliminary Results In Canine Experimental Arteriovenous Fistulas*, Radiology, Apr. 1999, 211:1, pp. 169-175.

* cited by examiner

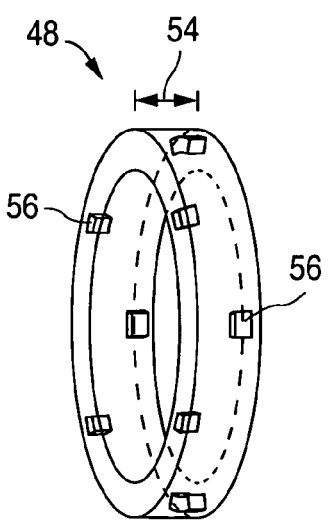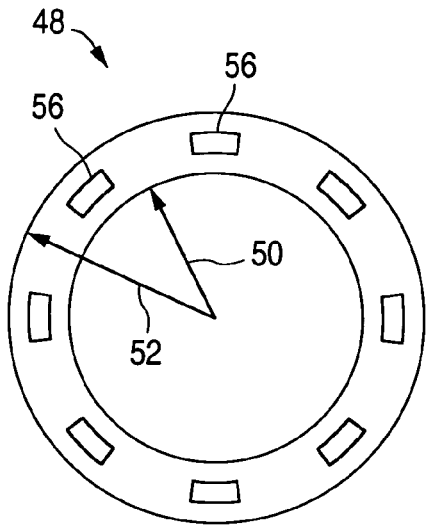
FIG. 7a  FIG. 7b
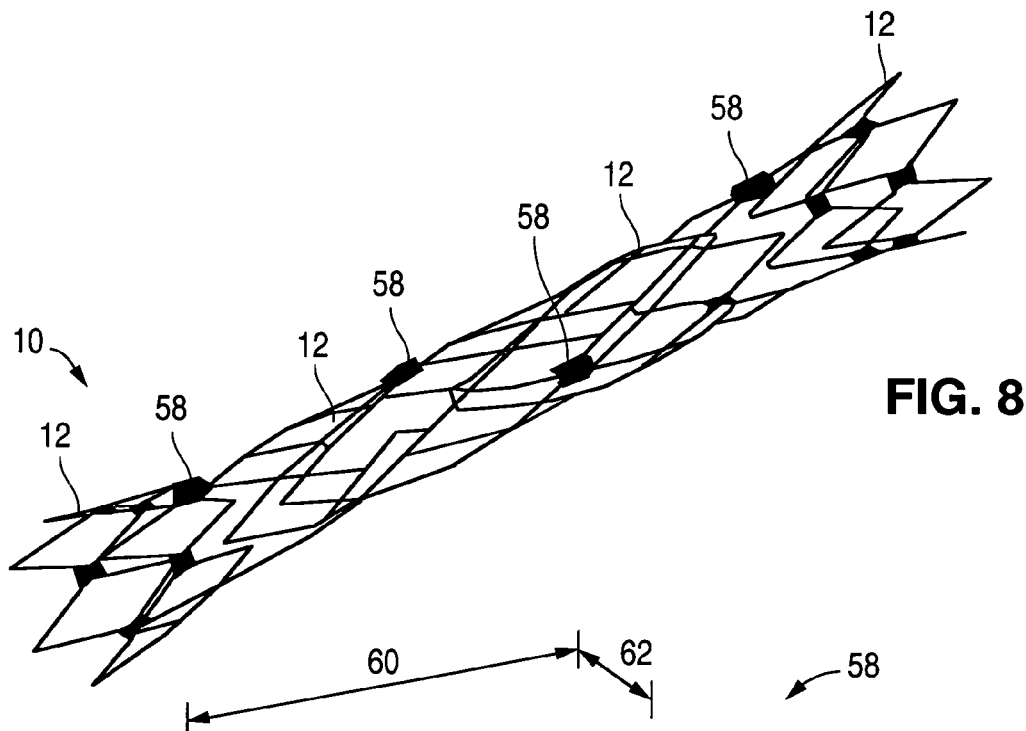
FIG. 8
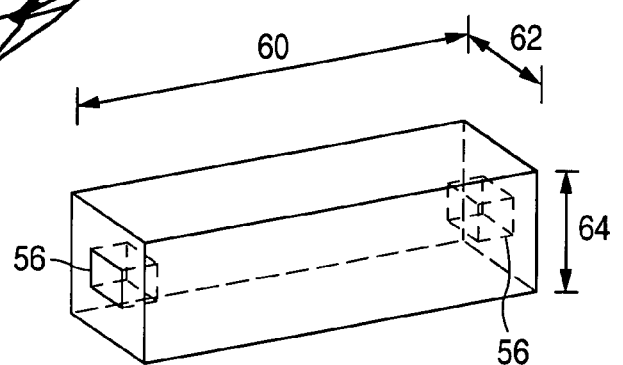
FIG. 9

FLEXIBLE STENT AND METHOD OF MAKING THE SAME

CROSS REFERENCE

This application is a divisional application of Ser. No. 10/108,778 filed on Mar. 26, 2002 now U.S. Pat. No. 7,288,111.

TECHNICAL FIELD

This invention relates to expandable intralumenal prostheses, commonly known as stents.

BACKGROUND OF THE INVENTION

Stents are used to treat occlusions in body vessels. Stents can be grouped based on their method of deployment: balloon expandable or self-expandable. Normally a balloon expandable stent is radially compressed onto a non-compliant balloon. The balloon expandable stent has a high radial strength, but when compressed it remains in the compressed state. When the balloon is inflated, the stent radially expands and maintains its shape after the deflation of the balloon. Balloon expandable stents are advantageous because they can be easily deformed for use in locations of curvature or where side branch access is required. Balloon expandable stents can also produce a higher radial force than self-expandable stents during deployment due to the physician's ability to control the pressure applied to the dilatating balloon. Tailoring the applied radial force during deployment can aid vascular remodeling of a hardened atherosclerotic vessel.

Self-expanding stents are "shape set" to the shape desired once deployed in the vessel. They are then compressed and constrained into a delivery shape, usually by a concentric sleeve containing the stent. The stent is then delivered to the desired location and the sleeve is removed. Upon removal of the sleeve, the stent returns to its "shape set" shape.

In U.S. Pat. Nos. 5,855,597 and 6,162,245, Jayaraman teaches a stent with self-expanding ends and a balloon-expanding middle. The stent can be attached externally or internally to a polyester fabric or extruded polytetraflouroethylene (PTFE) graft. The stent can also be extruded such that the stent and extruded tubes are jointly extruded together. The stent can be the middle layer of an extruded tube. Further, the stent may or may not be welded together. The stent can be placed at equal distances to each other on the surface of the graft and then attached to the graft by any suitable mechanism such as using sutures or adhesives.

In U.S. Pat. No. 6,168,621, Vrba teaches a stent with a self-expanding part at each end of a balloon expanding part. The self-expanding part is made from a shape memory metal, such as nitinol, so as to enable self-expansion at body temperature upon release of the stent from its delivery catheter.

In U.S. Pat. No. 6,315,708, Salmon et al. teach a stent with self-expandable sections at both ends of a balloon expandable section. The stent can be formed from nitinol by having different heat treatments for the central, balloon-expandable section as compared to the end, self-expandable sections. The stent could also be formed by having stainless steel for the central section of the stent and welding on nitinol end sections.

Regardless of the type of stent used, vascular plaque (e.g., atherosclerotic plaque) can be dislodged from the vessel wall during stent placement. The thrombi can form emboli that occlude vessels, leading to severe trauma such as strokes. Accordingly, it is desired to produce a stent that minimizes the risk of emboli production and that can capture thrombi.

During minimally invasive percutaneous deployment procedures, stents are often guided through tortuously curved and complex vasculature. The final location of the stent can also be along a length of vessel that curves sharply. Accordingly, a stent having a flexible body which can contort to the curvature of a vasculature is needed.

SUMMARY OF THE INVENTION

In accordance with one aspect of the embodiments of the invention, a stent for biological lumen placement is provided. The stent can include a first member having a proximal section, a second member having a distal section, and a connector joining the proximal section of the first member to the distal section of the second member. The connector can be made from a material comprising a polymer. The connector can also flexibly join the first member to the second member. The first member can be self-expandable and the second member can be capable of expanding with the application of an external force.

In one embodiment of the present invention, the first member and the second member can have a diamond shape and can be positioned next to each other along a longitudinal axis of the stent. In another embodiment, the first member and the second member can have zig-zag-shaped annular bands. In a further embodiment of the present invention, the connector can have a ring-shaped structure connected to the first member at a first end of the ring-shaped structure and to the second member at a second end of the ring-shaped structure. In yet another embodiment, the connector can be defined by a plurality of joint elements such that a corner of the first member is connected to an adjacent corner of the second member by one of the joint elements, and the joint elements can have a generally box-shaped structure.

In accordance with another aspect of the embodiments of the present invention, an implantable prosthesis is provided. The prosthesis can include a polymeric layer containing a self-expandable first ring member and a second ring member that can be expanded with the application of an external force. The first ring member can be positioned at a distance away from the second ring member.

In one embodiment of the present invention, the first ring member can be positioned at a first end of the prosthesis, the second ring member can be positioned between the first end and a second end of the prosthesis. In one embodiment, a self-expandable third ring member can be provided and positioned at the second end of the prosthesis. In another embodiment, the polymeric layer has a void-to-volume ratio of less than about 5%. In yet another embodiment, the prosthesis has a luminal layer having a void-to-volume ratio of about 40% to about 90% disposed on the inner surface of the polymeric layer. In a further embodiment, the prosthesis has an outer layer having a void-to-volume ratio of about 40% to about 90% disposed on the outer surface of the polymeric layer.

In accordance with another aspect of the embodiments of the present invention, a method for manufacturing a stent is provided. The method of manufacturing can include forming a band made at least in-part from polymer on a mandrel, positioning an end of a first member on a first end of the band, positioning an end of a second member on a second end of the band, and increasing the thickness of the band to encapsulate the ends of the first and second members. This method of manufacturing can flexibly connect the first member to the second member.

SUMMARY OF THE FIGURES

FIGS. 7a and 7b illustrate perspective and front views, respectively, of a polymer ring from an embodiment of the stent.

FIG. 8 illustrates a perspective view of another embodiment of the stent.

FIG. 9 illustrates a perspective view of one embodiment of a polymer connector from FIG. 8.

DETAILED DESCRIPTION

Apparatus

Embodiment with Polymer Layer

Figure 1:
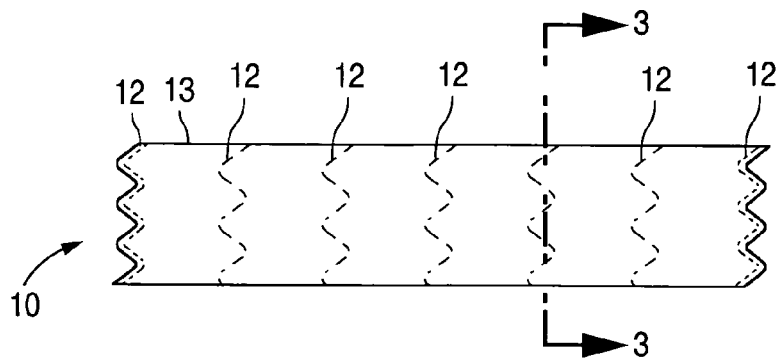
FIG. 1 illustrates a side view of one embodiment of the stent.

FIG. 1 illustrates an embodiment of a stent 10 that can have individual, disconnected structural rings 12 flexibly connected to one another by a polymer layer 13. The structural rings 12 can be a combination of balloon expandable structural rings 12 and self-expandable structural rings 12 or can all be the same type of structural ring 12 (i.e., all balloon expandable or all self-expandable). The stent 10 can have a length of about 0.5 cm (0.2 in.) to about 30 cm (10 in.), for example about 3 cm (1 in.).

Figure 2A:
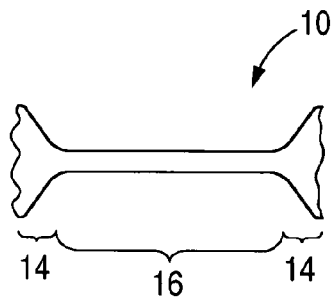
FIGS. 2a-2c illustrate various embodiments of the stent with the self-expandable rings expanded and the balloon expandable rings compressed.
Figure 2B:
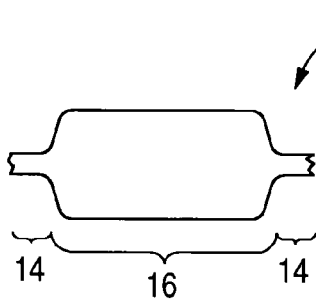
Figure 2C:
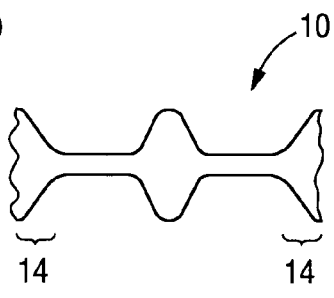

FIGS. 2a-2c show three separate embodiments of the stent 10 with the self-expandable structural rings 12 expanded and the balloon expandable structural rings 12 collapsed. The embodiment illustrated in FIG. 2a can have self-expandable structural rings 12 at end sections 14 and balloon expandable structural rings 12 in a middle section 16. During deployment, this embodiment can create an isolated space between the stent 10 and the wall of the vessel in order to capture thrombi that can be dislodged during the procedure. The number of the structural rings 12 can vary from about 1 to about 10 per centimeter of length of the stent 10, more narrowly from about 2 to about 5 per centimeter of length of the stent 10. Any combination of numbers of the self-expandable and the balloon expandable structural rings 12 can, however, be used, for example five balloon expandable structural rings 12 in the middle section 16 and one self-expandable structural ring 12 at each end section 14.

FIG. 2b illustrates an embodiment that can have balloon expandable structural rings 12 at the end sections 14 and self-expandable structural rings 12 in the middle section 16. During deployment, the radial force exerted by the balloon expandable structural rings 12 can be more easily controlled than that of the self-expandable structural rings 12. The end sections 14 can securely anchor to the vessel wall while the middle section 16 allows for sufficient contact or pressure against the vessel wall so as to minimize stress and potential damage to the vessel wall as compared to the end sections 14.

FIG. 2c illustrates an embodiment that can have self-expandable end sections 14 and a self-expandable structural ring or rings 12 in or near the middle of the stent 10 with the remainder of the structural rings 12 being balloon expandable. The stent 10 can create a pair of spaced regions between the stent 10 and the vessel wall during deployment.

Figure 3A:
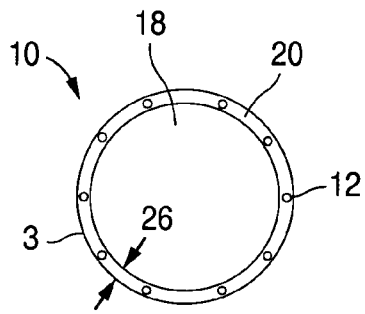
FIGS. 3a-3c illustrate embodiments of cross section 3-3 of FIG. 1.
Figure 3B:
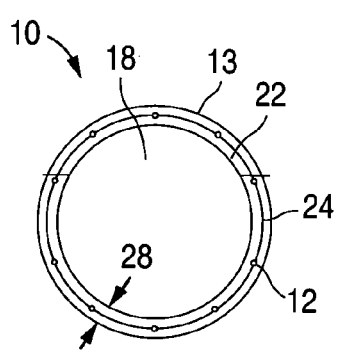

The polymer layer 13 can define a lumen 18 and can be made of a single layer 20 surrounding the structural rings 12 (FIG. 3a) or an inner sub-layer 22 and an outer sub-layer 24 surrounding the structural rings 12 (FIG. 3b). A thickness 26 of the single layer 20 or a combined thickness 28 of the inner sub-layer 22 and the outer sub-layer 24 can be about 10 microns (0.4 mils) to about 200 microns (8 mils), more narrowly of about 50 microns (2.0 mils) to about 75 microns (3.0 mils).

The polymer layer 13 can serve to hold the structural rings 12. The polymer layer 13 can compress intimal tears against the inner wall of the vessel to prevent occlusion of the vessel and can help trap thrombi between the stent 10 and the wall of the vessel. The polymer layer 13 further increases the flexibility of the stent 10—particularly as compared to rigid stents having structural rings 12 connected by stiff interconnecting members or welds—to aid deployment in curved vessels and reduce the mechanical stress applied to the structural rings 12 by the radial expansion of the stent 10. The polymer layer 13 can also provide better biocompatibility than a bare stent. Further, the polymer layer 13 can reduce unnatural blood flow around the stent 10. The polymer layer 13 can also act as an anchor for intimal growth and a matrix for drug delivery.

The polymer layer 13 can be made from any polymeric material including non-porous polyurethanes, porous polyurethanes (e.g., Thoralon®, available from Thoratec Corporation in Pleasanton, Calif.), PTFE, expanded PTFE (ePTFE), polyethylene tetraphthalate (PET), aliphatic polyoxaesters, polylactides, polycaprolactones, and hydrogels. "Hydrogel" is intended to include a cross-linked polymer, via covalent, ionic, or hydrogen bonding, to form a three-dimensional open lattice structure which is capable of entrapping water molecules to form a gel. Examples of hydrogels include non-permissive hydrogels such as anionic hydrogels (e.g., alginate or carageenan) and "solid" hydrogels (e.g., agarose or polyethylene oxide).

The polymer layer 13 can be substantially or completely non-porous. The polymer layer 13 can also have a void-to-volume ratio of less than about 5%, more narrowly less than about 1%. "Void-to-volume ratio" is defined as the volume of the pores divided by the total volume of the layer including the volume of the pores. Void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity.

Figure 3C:
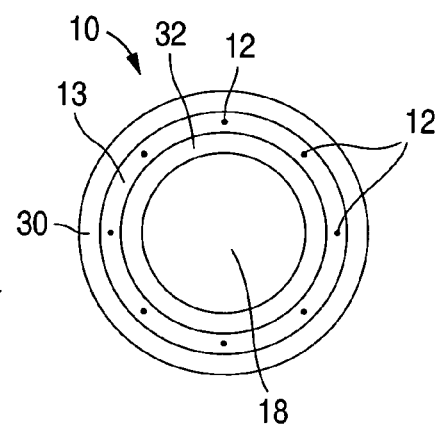

FIG. 3c illustrates an embodiment of the stent 10 having a porous outer layer 30 on the outer or tissue-contacting side of the polymer layer 13, the polymer layer 13, and a porous lumenal layer 32 on the lumen-side of the polymer layer 13. The porous outer layer 30 can be made of any suitable porous biocompatible material, either bioabsorbable (i.e., biodegradable) or biostable (i.e., non-biodegradable) in nature. Representative examples of materials that can be used for the porous outer layer 30 include those materials that can be used for the polymer layer 13.

Therapeutic substances can also be coated onto or contained within the porous outer layer 30 for sustained release subsequent to the implantation procedure. Intimal cell ingrowth can also be facilitated by the porous outer layer 30. The porous outer layer 30 also provides the stent 10 with a lubricious surface that decreases adhesion of the material of the porous outer layer 30 to itself while collapsed and reduces the degree of friction between the stent 10 and a delivery device.

The porous outer layer 30 can have a thickness of about 10 microns (0.4 mils) to about 50 microns (2 mils), more narrowly of about 20 microns (0.8 mils) to about 30 microns (1 mil). The porous outer layer can have a void-to-volume from about 40% to about 90%, more narrowly from about 70% to about 80%, for example about 76%, and an average pore diameter from about 1 micron (0.04 mils) to about 400 microns (20 mils), more narrowly from about 1 micron (0.04 mils) to about 75 microns (3.0 mils), including the range of about 1 micron (0.04 mils) to about 38 microns (1.5 mils).

The porous lumenal layer 32 can be made of any suitable porous biocompatible material, either bioabsorbable or biostable in nature. Examples of appropriate materials can be the same as those materials that can be used for the polymer layer 13. The porous lumenal layer 32 can also be used for therapeutic substance delivery by being coated with therapeutic substances or having therapeutic substances embedded in the matrix.

The porous lumenal layer 32 can have a thickness of about 10 microns (0.4 mils) to about 50 microns (2 mils), more narrowly of about 20 microns (0.8 mils) to about 30 microns (1 mil). The porous lumenal layer 32 can have a void-to-volume from about 40% to about 90%, more narrowly from about 65% to about 80%, for example about 72%, and an average pore diameter from about 1 micron (0.04 mils) to about 400 microns (20 mils), more narrowly from about 1 micron (0.04 mils) to about 75 microns (3.0 mils), including the range of about 1 micron (0.04 mils) to about 38 microns (1.5 mils).

Figure 4:
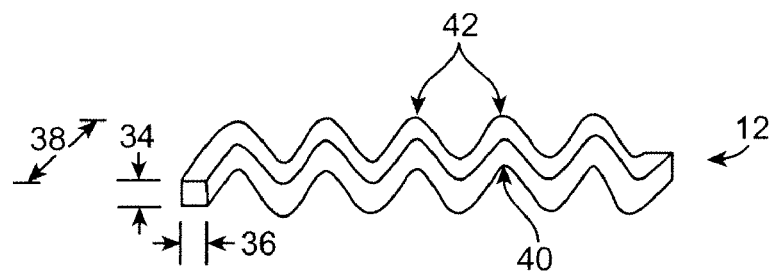
FIG. 4 illustrates a perspective view of an elongated structural ring from an embodiment of the stent.

FIG. 4 illustrates an embodiment of a zig-zag-shaped self-expandable or balloon expandable structural ring 12 that has been cut and flattened into a plane for illustrative clarity. The structural ring 12 can have a structural ring height 34 from about 0.005 mm (0.0002 in.) to about 1 mm (0.04 in.), for example about 0.15 mm (0.0059 in.). The structural ring 12 can have a structural ring width 36 from about 0.05 mm (0.002 in.) to about 1 mm (0.04 in.), for example about 0.15 mm (0.0059 in.). The structural ring 12 can have a structural ring depth 38 from about 1 mm (0.4 in.) to about 10 mm (4 in.), more narrowly about 2.5 mm (0.098 in.) to about 5 mm (0.2 in.). The structural ring 12 can have a number of crowns 40 (e.g., sharp turns) from about three to about ten, for example, about five to about seven. The structural ring 12 can also have a crown inner radius 42 from about 0.05 mm (0.002 in.) to about 1 mm (0.04 in.), for example 0.2 mm (0.008 in.).

"Balloon-expandable" structural rings 12 can be defined as the structural rings 12 that can only expand from a collapsed position to their designed deployed dimension with the application of an external force. The balloon expandable structural rings 12 can provide sufficient structural support so as to maintain vascular patency when the stent 10 is deployed. Representative materials that can be used for balloon expandable structural rings 12 include metals, for example titanium-nickel alloys (e.g., nitinol), tantalum alloys, cobalt chrome alloys (e.g., Elgiloy), platinum/tungsten alloys, stainless steels and combinations thereof, and polymers. Balloon expandable structural rings 12 within the same stent 10 can be made from different materials.

"Self-expandable" structural rings 12 can be defined as any expandable structural rings 12 that do not qualify as balloon expandable structural rings 12. The structure and dimensions of the self-expandable structural rings 12 can be the same as the structure and dimensions of the balloon expandable structural rings 12 described above and illustrated in FIG. 4. Self-expandable structural rings 12 should be able to provide sufficient structural support to maintain vascular patency and anchor the stent 10 against the vessel so as to seal the space between the balloon expandable structural rings 12 and intima in order to trap thrombi. Materials that can be used for self-expandable structural rings 12 can be the same as those described above for balloon expandable structural rings 12. Self-expandable structural rings 12 within the same stent 10 can be made from different materials.

Four characteristics of the structural rings 12 include: (1) the yield stress of the material used; (2) the modulus of elasticity of the material used; (3) the desired compressed diameter; and (4) the desired expanded diameter. These characteristics can be determinative of whether the structural rings 12 are balloon expandable or self-expandable. Since these four characteristics are interrelated, analyzing any single characteristic is most clearly done when the other three characteristics are held constant. For example, compared with the self-expandable structural rings 12, the balloon expandable structural rings 12 can have smaller yield stresses while holding moduli of elasticity, the desired compressed diameters, and the desired expanded diameters constant. Compared to the self-expandable structural rings 12, the balloon expandable structural rings 12 can have smaller moduli of elasticity while holding the other three characteristics constant. Likewise, the analysis follows that as compared to self-expandable structural rings 12, balloon expandable structural rings 12 can have smaller compressed diameters while holding the other three characteristics constant, and larger expanded diameters while holding the other three characteristics constant.

Embodiment With Polymer Rings

Figure 5:
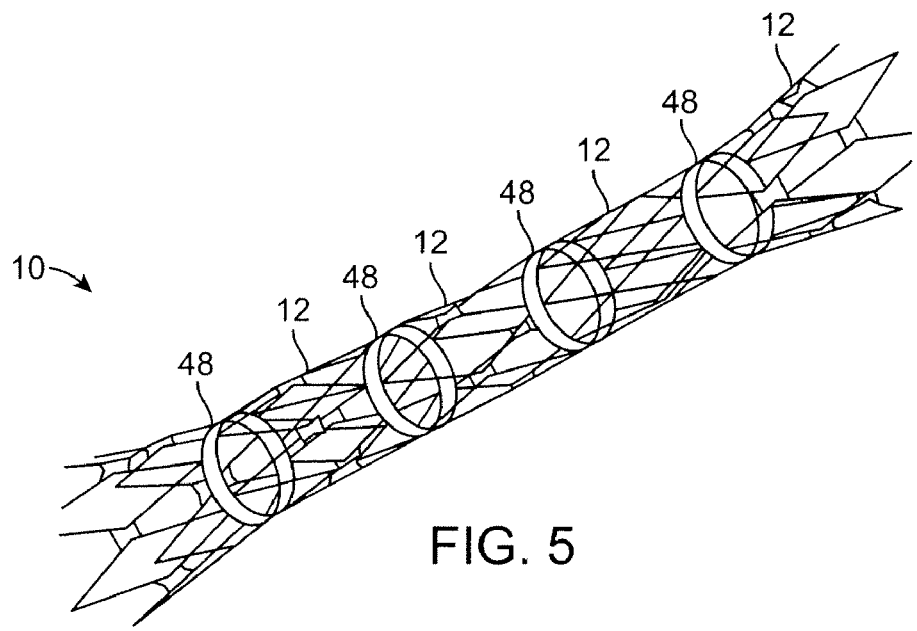
FIG. 5 illustrates a perspective view of another embodiment of the stent.
Figure 6:
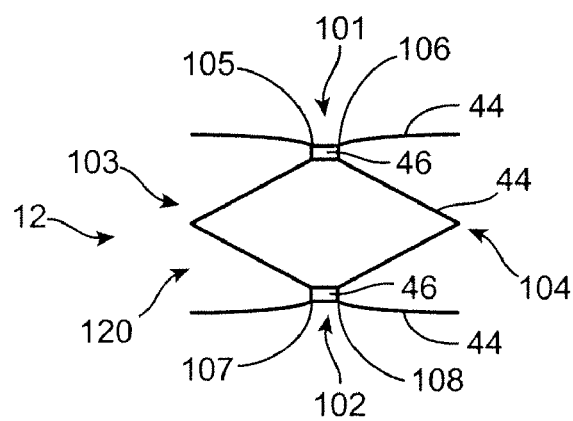
FIG. 6 illustrates a side view of an embodiment of an expandable structural ring from FIG. 5.

FIG. 5 illustrates another embodiment of the stent 10. The stent 10 can have expandable structural rings 12 made from zig-zag-shaped annular bands (or ring members) 44 forming diamond shapes 120 as shown in FIGS. 5-6. The zig-zag-shaped annular bands 44 can be joined by connecting points 46. The connecting points 46 can be a bridge of the material, adhesives, or welds, between the zig-zag-shaped annular bands 44. Referring to FIG. 6, the structural diamond shape 120 has a first corner 101, a second corner 102, a third corner 103 and a fourth corner 104. The first corner 101 is formed by a first pair 105, 106 of adjacent bend sections connected to each other by a first connecting point 46. The second corner 102 is formed by a second pair 107, 108 of adjacent bend sections connected to each other by a second connecting point 46. The third corner 103 and fourth corner 104 of the diamond shape 120 are formed by opposed bend sections that are between the first pair 105, 106 and the second pair 107, 108 of adjacent bend sections. The structural rings 12 can be made from any number of the zig-zag-shaped annular bands 44 and can be held to one another by polymer rings 48. Structural rings 12 in FIG. 5 have a diamond shape and are positioned adjacent to each other along a longitudinal axis of the stent 10. The rings 12 are connected by the ring-shaped polymer ring 48.

The structural rings 12 can be balloon expandable or self-expandable. The annular rings can have about 4 to about 25 bend sections, for example about 5 bend sections per ring. The function and materials for the structural rings 12 in this embodiment can be the same as the function and materials for the structural rings 12 in the embodiment with the polymer layer 13 described above.

FIGS. 7a and 7b illustrate an embodiment of the polymer rings 48. The polymer rings 48 can be circumferentially continuous and can have mounting sockets 52 where the structural rings 12 can attach to the polymer rings 48. The mounting sockets 52 can be lined with an elastic material and/or a material with a higher coefficient of friction than the material of the polymer rings 48 in order to help grip the structural rings 12. The number of mounting sockets 52 per polymer ring 48 can be the same as the number of bend sections per structural ring 12. The mounting sockets 52 should not interfere with the structural integrity of the polymer ring 48.

In a relaxed state, the polymer rings 48 can have a ring length 54 from about 0.5 mm (0.02 in.) to about 1 cm (0.4 in.), more narrowly from about 1 mm (0.04 in.) to about 3 mm (0.1 in.). The polymer rings can have a ring thickness 56 from about 10 microns (0.4 mils) to about 200 microns (8 mils), more narrowly from about 20 microns (0.8 mils) to about 30 microns (1 mil).

The polymer rings 48 can serve to provide flexibility to the stent 10. The polymer rings 48 can also be made from the same materials as the polymer layer 13 described above. The polymer rings 48 within a single stent 10 can have different dimensions and different materials to vary the flexibility along the length of the stent 10.

Embodiment With Connections

FIG. 8 illustrates yet another embodiment of the inventive stent 10 having connections between the structural rings 12. The connections can be discreet polymer connectors 58, including the block-shaped connector illustrated in FIG. 9. Each end of the discreet polymer connectors 58 can have any number of mounting sockets 56, for example about one for connecting adjacent struts 44 of the stent 10.

The polymer connectors 58 can have a connector length 60 from about 0.5 mm (0.02 in.) to about 10 mm (0.4 in.), for example about 2 mm (0.08 in.). The polymer connector 58 can have a connector width 62 ranging from about 0.5 mm (0.02 in.) to about 10 mm (0.4 in.), for example about 2 mm (0.08 in.). The polymer connector 58 can have a connector depth 64 ranging from about 0.005 mm (0.0002 in.) to about 1 mm (0.04 in.).

The polymer connectors 58 can serve to provide flexibility to the stent 10. The polymer connectors 58 can also be made from any material described above for the polymer layer 13. The polymer connectors 58 of a single stent 10 can have different dimensions and can be made from different materials to vary the flexibility along the length and along the angular position of the stent 10.

Method of Manufacture

Structural Rings

The structural rings 12 can be selected from those commercially available or can be manufactured by cutting, for example by laser drilling, from a solid tube or flat plate of a desired material. If the structural ring 12 is cut from a flat plate, the cut piece can then be wrapped around a cylindrical mandrel and the ends of the cut piece can be joined by any conventional method such as heat welding, pressure welding, or attaching with an adhesive. The structural ring 12 can then be etched by any method known to one having ordinary skill in the art. The etching can be performed to remove a brittle oxide layer on the surface of the structural ring 12.

The expanded shape of the self-expandable structural rings 12 can be pre-set in an annealing process. The self-expandable structural rings 12 can be mounted on a mandrel simulating the desired final shape of the self-expandable structural rings 12. The self-expandable structural rings 12 can then be heated for a time and at a temperature to increase grain size and then cooled to recrystalize the material of the self-expandable structural rings 12 in a desired phase. The mechanical properties of the self-expandable structural rings 12, including modulus of elasticity and plateau stress, can vary based on the heat treating time and temperature. The material and dimensions can also be determinative of the annealing time and temperature. For example, a nitinol stent on a reshaping mandrel can be heat treated at about 460° C. for about 15 minutes. A nitinol stent on a reshaping mandrel can, however, also be heat treated at about 460° C. for about 5 minutes, thus producing different mechanical characteristics for the self-expandable structural rings 12, including a higher modulus of elasticity and plateau stress, than the self-expandable structural rings 12 heated for about 15 minutes. Annealing times and temperatures for different materials and the production of different characteristics are known to one having ordinary skill in the art.

Stent With Polymer Layer(s)

To manufacture an embodiment of the stent 10 having the polymer layer 13, an inert (e.g., glass) mandrel can be immersed or sprayed with a composition to form the polymer layer 13. The mandrel can be, for example, about 6 mm (0.2 in.) in diameter and can be cleaned with isopropyl alcohol. First the composition can be prepared by dissolving the polymer in a solvent by any conventional method. Any suitable solvent can be used including alcohols, aromatic hydrocarbons, dimethyl acetamide (DMAC), and the like. Depending on the application method, the polymer can comprise greater than 0% to below about 100% by weight of the total weight of the composition. The specific amount depends on a variety of factors, including the type of polymer used and the viscosity desired. Using Thoralon® as the polymer and DMAC as the solvent, the polymer can comprise about 5% to about 40% by weight of the total weight of the composition. The polymer can be less than about 5% by weight for some spray application procedures. In one embodiment where the mandrel is immersed in the composition, the polymer can be about 24% by weight of the total weight of the composition.

In one embodiment, the mandrel can be immersed in the composition at a speed of about 70 cm/min (30 in./min) through a die (having, for example, a diameter of about 6.76 mm (0.266 in.). The solvent can then be removed or allowed to evaporate to form a film layer of the polymer on the mandrel. The step of removing the solvent need not be taken to completion so as to provide a polymer layer with a semi-solid surface. The semi-solid surface can provide a better adhesive tie between multiple coating applications which, in essence, eliminates a distinct seam between the multiple layers. Conversely, taking the solvent removal to completion can create a seam, creating the inner sub-layer 22 and the outer sub-layer 24 (see FIG. 3b). Evaporation of the solvent can be induced by application of heat treatment for about 5 minutes to about 24 hours in an oven having a temperature of about 25° C. to about 80° C. In one exemplary embodiment, evaporation can be induced at about 60° C. for about 60 minutes, and at ambient pressure. Alternatively, vacuum conditions can be employed.

Following the formation of a first coat of the polymer layer 13, the structural rings 12 can be placed on the mandrel and securely positioned on the first coat. The composition can then be applied again to cover the structural rings 12. In one embodiment, this second application of the composition can be performed by immersing the mandrel in the composition at a speed of about 70 cm/min (30 in./min) through a die (having, for example, a diameter of about 7.24 mm (0.285 in.)). Subsequent to the application of the second coat of the composition, the solvent can be removed or allowed to evaporate to form the polymer layer 13 that encapsulates the structural rings 12.

Porous Lumenal Layer

In embodiments with the porous lumenal layer 32, the mandrel can be first immersed in a composition or, alternatively, the mandrel can be sprayed with the composition for forming the porous lumenal layer 32. The composition can constitute at least one of the aforementioned polymers admixed with a solvent. Using Thoralon® as the polymer and DMAC as the lumenal layer solvent, the composition can include the previously described polymer/solvent weight ratios. In one embodiment where the mandrel is immersed in the composition, the polymer can be about 14% by weight of the total weight of the composition.

Porosity can be introduced by adding water-soluble particles, such as salt, to the composition before the composition is applied to the mandrel. In one embodiment, the particles can be mixed into the composition with a spinning blade mixer for about an hour under ambient pressure and in a temperature range of about 18° C. to about 27° C. The particles can then be extracted by soaking the dried layer in distilled water and dissolving the particles, leaving pores behind. The resulting void-to-volume can be substantially equal to the ratio of salt volume to the volume of the polymer plus the salt. The resulting pore diameter can also be substantially equal to the diameter of the salt grains. Extraction can occur through a variety of methods known to those having ordinary skill in the art, including soaking in a substantially still distilled water at about 60° C. for about one hour while on a mandrel, and soaking in substantially still distilled water at about 60° C. for about one hour while off the mandrel. Extraction can occur once all the layers have been applied to the sent 10. The composition can have an amount of salt of about 10 to about 20 times, for example about 14 times, the amount of polymer by weight.

In one embodiment, the mandrel can be immersed in the composition at a speed of about 70 cm/min (30 in./min) through a die (having, for example, a diameter of about 6.76 mm (0.266 in.)). Subsequent to the application of the composition, the solvent can be removed or allowed to evaporate to form a film layer of the polymer on the mandrel. Evaporation can be induced by application of heat treatment, for example, about 5 minutes to about 24 hours in an oven at a temperature of about 25° C. to about 80° C. For example, heat treatment can be conducted at about 60° C. for about 20 minutes at ambient pressure. Alternatively, vacuum conditions can be employed. The process of application of the composition and removal of the solvent can be repeated to form the porous lumenal layer 32 of any suitable thickness.

Porous Outer Layer

In embodiments with a porous outer layer 30, a composition can be applied to the polymer layer 13 for forming of the porous outer layer 30. The solvent used with the composition can be capable of wetting the polymer layer 13 to aid bonding of the two layers. The ratio of polymer to solvent for the composition can be the same as the previous ratios. In one embodiment where the mandrel is immersed in the composition, the polymer can be about 10% by weight of the total weight of the composition.

The composition can also include particles to form pores. The composition can have an amount of salt about 1 to about 10 times, for example about 6 times, the amount of polymer by weight.

In one embodiment, the mandrel can be immersed in the composition at a speed of about 70 cm/min (30 in./min) through a die (having, for example, a diameter of about 7.24 mm (0.285 in.)). Subsequent to the application of the composition, the solvent can be removed or allowed to evaporate to form the porous outer layer 30. The process of application of the composition and removal of the solvent can be repeated to form the porous outer layer 30 of any suitable thickness.

Stent With Polymer Rings or Polymer Connectors

To manufacture an embodiment of the stent 10 having the polymer rings 48 or the polymer connectors 58, the polymer rings 48 or the polymer connectors 58 can first be cast or otherwise formed by techniques known to one having ordinary skill in the art. The structural rings 12 can then be press fit into the mounting sockets 56. An adhesive can also be applied where the structural rings 12 contact the polymer rings 48 or the polymer connectors 58.

Figure 10A:
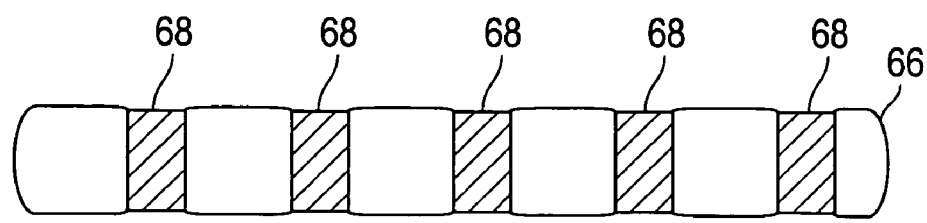
FIGS. 10a-10c illustrate a method of manufacturing an embodiment of the stent on a mandrel.
Figure 10B:
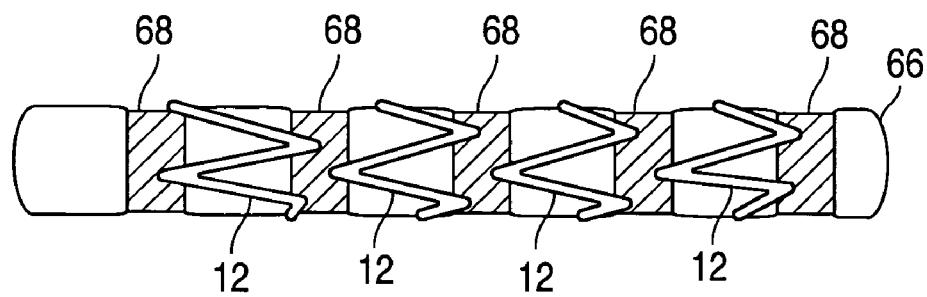
Figure 10C:
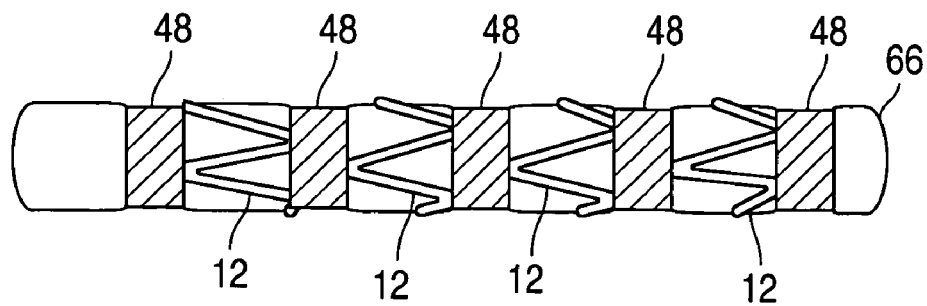

The stent 10 having the polymer rings 48 or the polymer connectors 58 can also be manufactured directly onto the mandrel 66. FIGS. 10a-10c illustrate a method for manufacturing the stent 10 with the polymer rings 48. An equivalent method can be used for forming the connectors 58. First, a composition for the polymer rings 48 can be prepared constituting at least one of the aforementioned polymers dissolved in a solvent. In one embodiment, the composition can be applied to the mandrel 66 by a syringe to form a desired number of band layers 68. The syringe can have, for example, a 20 gauge needle tip for controlling the application of the composition. The solvent can then be removed from the composition.

Following the formation of the band layers 68, the structural rings 12 can then be placed on the mandrel 66 such that a section of the structural rings 12 overlaps and is positioned over on the band layers 68, as illustrated in FIG. 10b. The composition is then applied by the syringe to complete the polymer rings 48, as illustrated in FIG. 10c.

Method of Using

Figure 11A:
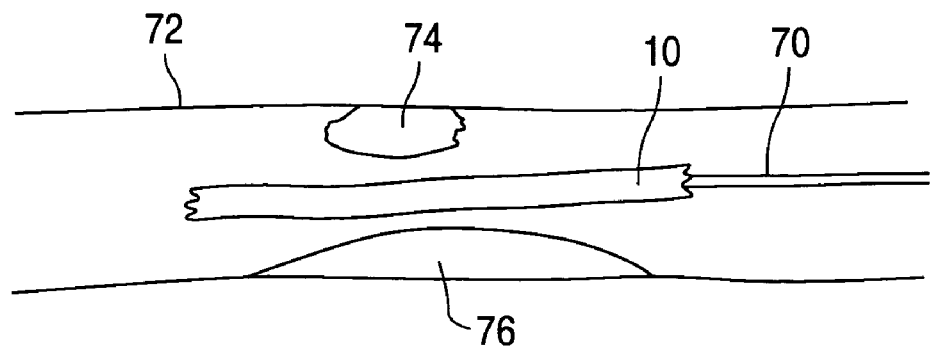
FIGS. 11a-11c illustrate a method of using an embodiment of the stent.
Figure 11B:
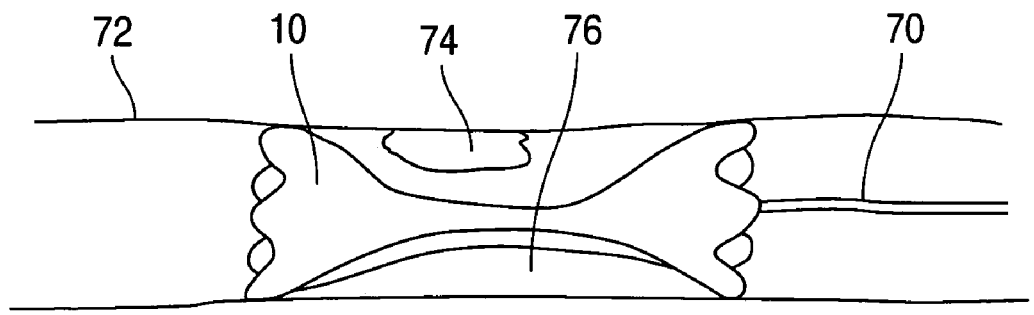
Figure 11C:
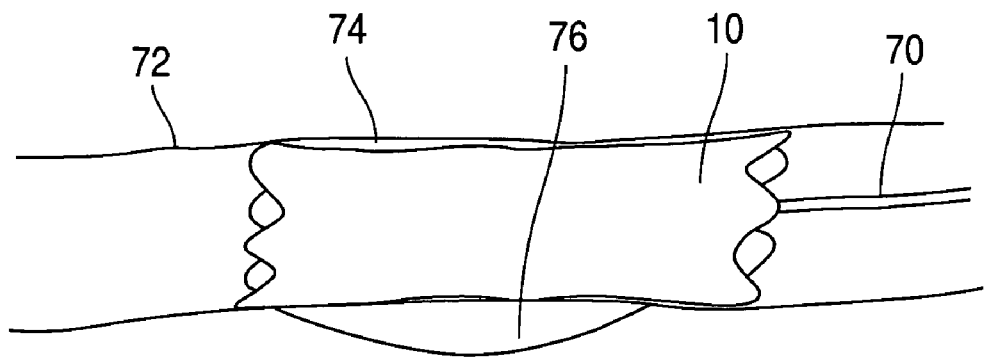

FIGS. 11a-11c illustrate a method of using one embodiment of the stent 10. FIG. 11a illustrates the stent 10 after having been radially compressed and loaded onto a delivery device 70, for example a catheter, and then positioned in a blood vessel 72 at the desired deployment location, for example near an intimal flap 74 or atherosclerotic plaque 76. As illustrated in FIG. 11b, the delivery device 70 can then release the self-expandable end sections 14. The self-expandable end sections 14 then segment the space between the stent 10 and the blood vessel wall from the rest of the blood vessel 72 in order to trap thrombi. In embodiments where the stent 10 is covered by the porous outer layer 30, the porous lumenal layer 32, or has the polymer layer 13, the space between the stent 10 and the blood vessel wall can be substantially isolated from fluid flow. The self-expandable end sections 14 can also minimize migration of the stent 10 during deployment by anchoring the stent 10 against the blood vessel wall at the beginning of the deployment process. A dilatation device can then radially expand the balloon expandable middle section 16, pressing and holding any obstructions against the wall of the blood vessel and performing vascular remodeling as necessary, as illustrated in FIG. 11c.

The structure of the stent 10 and the combination of balloon expandable and self-expandable structural rings 12 can be selected based on the intended location of the stent 10 within the body. For example, when the stent 10 is intended for coronary or neurovascular use, the stent 10 can have the structure illustrated in FIG. 8 and can be made from all balloon expandable structural rings 12 so as to facilitate the connection of side branches of the blood vessel 72 to the stent 10 by methods known to one having ordinary skill in the art. As another example, in order to minimize the effects of the stent 10 being crushed by external forces when the stent 10 is intended for peripheral vessel use, the stent 10 can have the structure illustrated in FIG. 5 and can be made from all self-expandable structural rings 12. In yet another example, when the stent 10 is intended for saphenous vein graft use, the stent 10 can have the structure illustrated in FIG. 5 and can be made from self-expandable and balloon expandable structural rings 12, for example in the configuration as illustrated in FIG. 2a.

Although the invention has been disclosed in terms of particular embodiments and applications, one of ordinary skill in the art, in light of this teaching, can generate additional embodiments and modifications without departing from the spirit of or exceeding the scope of the claimed invention. For example, the polymer rings 48 and the polymer connectors 58 can be used with the zig-zag-shaped structural rings 12. Similarly, the polymer layer 13 can be used with the multiple diamond-shaped struts 44. Accordingly, it is to be understood that the drawings and descriptions herein are proffered by way of example to facilitate comprehension of the invention and should not be construed to limit the scope thereof.

What is claimed is:

1. A stent, comprising:
a first member having a proximal section and including first and second zig-zag-shaped annular bands, each of the bands having bend sections, wherein the first and second bands are arranged to form a structural ring having a diamond-shape, the first member further including a plurality of connecting points that connect a portion of the bend sections of the first annular band with a corresponding portion of the bend sections of the second annular band;
a second member having a distal section; and
a connector joining the proximal section of the first member to the distal section of the second member, the connector being made from a material comprising a polymer;
wherein the connector flexibly joins the first member to the second member, and wherein the first member is self-expandable and the second member is capable of expanding with the application of an external force;
wherein the first member diamond shape has a first corner, second corner, a third corner and a fourth corner, the first member further including
a first pair of adjacent bend sections of the first and second annular bands connected to each other by a first connecting point and forming the first corner,
a second pair of adjacent bend sections of the first and second annular bands connected to each other by a second connecting point and forming the second corner, and
the third and fourth corners of the diamond shape are formed by opposed bend sections of the first annular band and the second annular band, wherein the opposed bend sections are between the first and second pairs of adjacent bend sections; and
wherein the first and second connecting points are one of a bridge of material, adhesive and weld.

2. The stent of claim 1, wherein the first member and the second member have a diamond shape and are positioned next to each other along a longitudinal axis of the stent.

3. The stent of claim 1, wherein the connector comprises a ring-shaped structure, the ring-shaped structure connected to the proximal section of the first member at a first end of the ring-shaped structure and to the distal section of the second member at a second end of the ring-shaped structure.

4. The stent of claim 1, wherein the connector is defined by a plurality of joint elements such that a corner of the first member is connected to an adjacent corner of the second member by one of the joint elements.

5. The stent of claim 4, wherein the joint elements have a generally box-shaped structure.

6. The stent of claim 1, wherein the connector comprises a ring connected to the proximal section of the first member at a first end of the ring and to the distal section of the second member at a second end of the ring-shaped structure.

7. The stent of claim 1, wherein the opposed bends are connected to polymer rings.

8. The stent of claim 1, wherein the first annular band has between four and twenty five bend sections.

9. A stent comprising:
a balloon expandable structural ring including:
a first ring member having a first bend section, a second bend section and a third bend section, wherein the second bend section is between the first and third bend sections;
a second ring member having a fourth bend section, a fifth bend section and a sixth bend section, wherein the fifth bend section is between the fourth and sixth bend sections;
a first connecting point connecting the first and fourth bend sections;
a second connecting point, separate from the first connecting point, connecting the third and sixth bend sections;
a polymer ring comprising a first socket and a second socket, the first socket being connected to the second bend; and
a self-expandable structural ring connected to the second socket.

10. The stent of claim 9, further including a second polymer ring comprising a third socket connected to the fifth bend section of the balloon expandable structural ring.

11. The stent of claim 10, wherein the second and fifth bend sections form opposed corners of a diamond shape.

12. The stent of claim 9, wherein the first wire strut and the second wire strut have zig-zag shapes.

13. An implantable prosthesis, comprising:
(a) a first ring member;
(b) a second ring member, the first ring member positioned at a distance away from the second ring member, wherein the first ring member and the second ring member are embedded within and connected exclusively by a non-porous polymeric layer, and wherein the first ring member is self-expandable and the second ring member expands with the application of an external force;

(c) a first porous polymeric layer disposed over a first side of the non-porous layer; and (d) a second porous polymeric layer disposed over a second opposing side of the non-porous polymeric layer; and wherein the second ring member is positioned at an end of the implantable member prosthesis and the first ring member is positioned at about a middle of the implantable prosthesis.

* * * * *